US005704073A

United States Patent [19]

Sword et al.

[11] Patent Number: 5,704,073

[45] Date of Patent: Jan. 6, 1998

[54] QUICK DONNING GOGGLES FOR USE WITH BREATHING MASK

[75] Inventors: Randall Jay Sword, Danvers; Jose Tadeo Vergara de Castro, Newton, both of Mass.; Imraan Aziz, Stanford, Calif.

[73] Assignee: Figgie International Inc., Willoughby, Ohio

[21] Appl. No.: 509,800

[22] Filed: Aug. 1, 1995

[51] Int. Cl.$^6$ .............................. A61F 9/02; A62B 18/02

[52] U.S. Cl. .............................. 2/427; 2/428; 128/206.23

[58] Field of Search .............................. 2/427, 428, 430, 2/452, 9, 206; 128/206.23, 201.17, 857

[56] References Cited

U.S. PATENT DOCUMENTS

| | | | |
|---|---|---|---|
| 2,669,717 | 2/1954 | Diggs | 2/9 |
| 3,298,031 | 1/1967 | Morgan | 2/9 |
| 3,707,966 | 1/1973 | Nebel | 128/212 |
| 3,806,949 | 4/1974 | Bushman | 2/414 |
| 3,971,368 | 7/1976 | Forbes et al. | 128/142 R |
| 4,172,455 | 10/1979 | Beaussant | 128/142.7 |
| 4,250,577 | 2/1981 | Smith | 2/427 |
| 4,361,145 | 11/1982 | Ekstrom et al. | 128/204.26 |
| 4,494,538 | 1/1985 | Ansite | 128/205.25 |
| 4,537,189 | 8/1985 | Vicenzi | 128/202.13 |
| 4,653,124 | 3/1987 | McNeal et al. | 2/427 |
| 4,905,684 | 3/1990 | Heffer | 128/202.13 |
| 5,261,398 | 11/1993 | Sobolik | 128/206.23 |
| 5,406,943 | 4/1995 | Hubbard et al. | 128/206.23 X |
| 5,406,944 | 4/1995 | Gazzara | 128/857 |
| 5,488,948 | 2/1996 | Dubruille et al. | 128/207.11 |

FOREIGN PATENT DOCUMENTS

| | | | |
|---|---|---|---|
| 0288391 | 10/1988 | European Pat. Off. . | |
| 625344 A2 | 11/1994 | European Pat. Off. | 2/427 |
| 2336096 | 7/1977 | France | 2/428 |
| 2607916 | 6/1988 | France . | |
| 2715572 | 8/1995 | France . | |
| 817167 | 7/1989 | United Kingdom . | |
| WO95/20995 | 8/1995 | WIPO . | |

*Primary Examiner*—Peter Nerbun

*Attorney, Agent, or Firm*—Hodgson, Russ, Andrews, Woods & Goodyear LLP

[57] ABSTRACT

A face mask for covering the nose and mouth of the wearer for supplying breathing gas thereto and a pair of strapless goggles which are easily and quickly donnable. The goggles are detachably attachable to the face mask by a tongue-and-groove connection wherein the tongue of the goggles is snapped into the face mask groove. Buttons are provided at the groove entrance for locking the tongue in the groove, the goggles being removable by depressing the buttons and sliding the tongue out over the depressed buttons. A face mask strap is coupled with hooks on the goggles frame for holding the goggles sealingly against the wearer's face. A vent is provided for supplying breathing gas to the goggles for venting thereof so as to prevent the entrance of smoke or disabling gases and to defog the lens.

5 Claims, 6 Drawing Sheets

FIG. 1

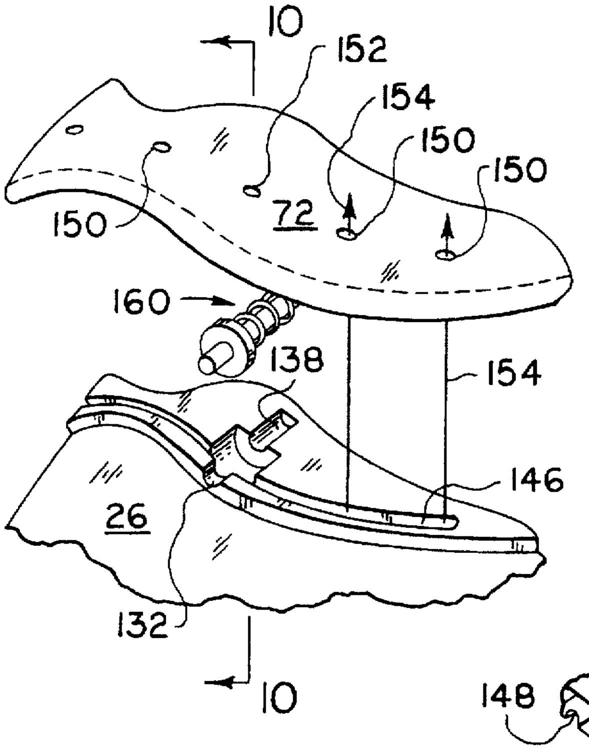
FIG. 8
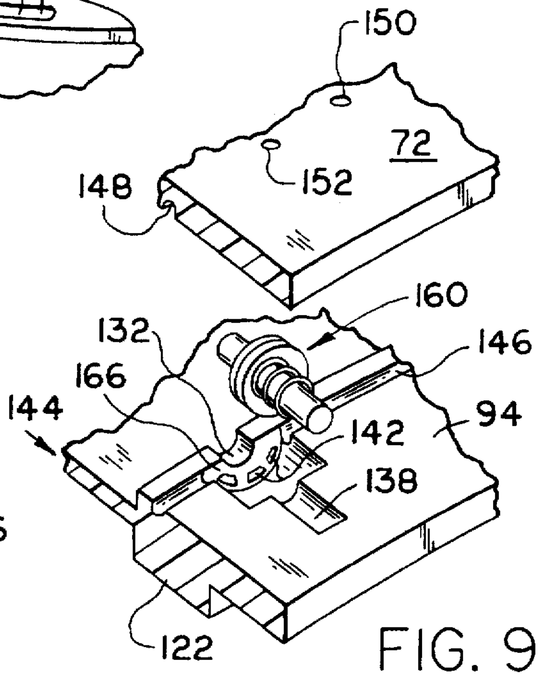
FIG. 9
FIG. 10
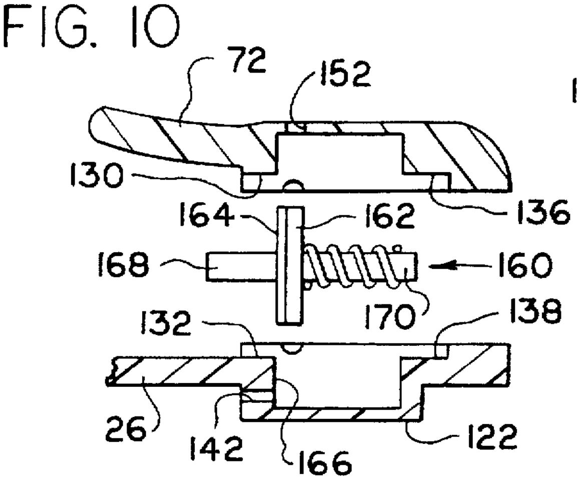
FIG. 11
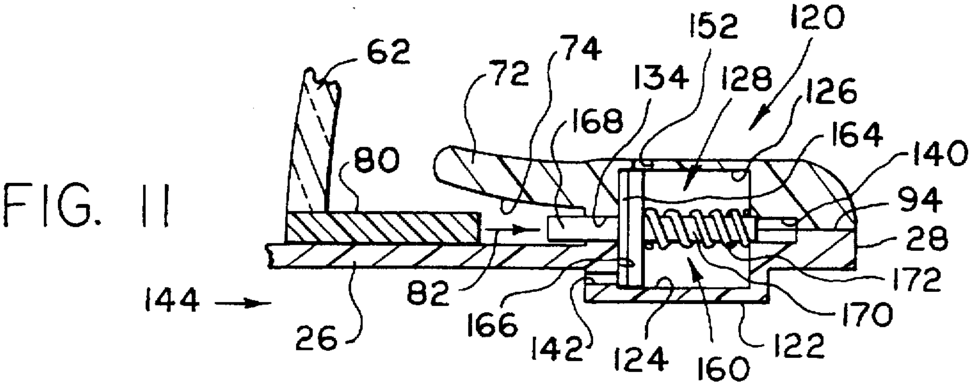

QUICK DONNING GOGGLES FOR USE WITH BREATHING MASK

The present invention relates generally to breathing masks such as worn by airplane pilots. More particularly, the present invention relates to the use of goggles with a half face mask, i.e., one which covers a wearer's nose and mouth for breathing but which does not cover the eyes.

Examples of face masks for various purposes are described in U.S. Pat. Nos. 3,707,966; 3,806,949; 3,971,368; 4,172,455; 4,361,145; 4,494,538; and 4,537,189. The disclosures of these patents are incorporated herein by reference. Such a mask is connected to a hose providing an oxygen supply and has an exhalation valve.

Federal rules may include requirements that pilots of specified airplanes wear an oxygen or breathing mask when flying above a certain altitude and under other circumstances and/or be able to quickly put one on in an emergency. Because a full face mask is inconvenient, uncomfortable, and may interfere with a pilot's functioning during normal flight, pilots generally prefer half face pieces, which typically include straps or other restraining means providing a head harness.

If there is smoke or fumes, the ability to see is also needed. The pilot, unless he or she is already wearing a full face mask, has two options. The half face piece may be removed and a full face mask put on. Alternatively, the half face piece may be left on and goggles donned.

Since the pilot may be busy with operating and/or emergency procedures, it is considered desirable that the goggles be easily and quickly donnable with only one hand.

U.S. Pat. Nos. 2,669,717; 3,298,031; 3,971,368; 4,250,577; 4,653,124; and 4,905,684 contain examples of face protector or face mask/goggles combinations. These combinations are unsuitable for the desired easy and rapid donning of goggles by a pilot already wearing a half face piece.

Accordingly, it is an object of the present invention to provide for quick and easy donning of goggles with one hand by a pilot or other person wearing a half face piece.

It is a further object of the present invention to provide for venting of the goggles so that disabling gases from the ambient air may be prevented from accumulating within the goggles.

It is yet another object of the present invention to provide a rugged, effective, reliable, and inexpensive combination of face mask and goggles therefor.

It is a still further object of the present invention to furnish the mask and goggles as an assembly so that the goggles may be left attached to the mask and the combination stowed as a full face mask assembly.

It is another object of the present invention to improve the wearer's field of vision.

In order to provide for quick and easy donning of goggles for a person wearing a breathing mask, in accordance with the present invention, the goggles are strapless and detachably attachable to the mask for holding the goggles sealingly against the wearer's face.

The above and other objects, features, and advantages of the present invention will be apparent in the following detailed description of the preferred embodiment thereof when read in conjunction with the accompanying drawings wherein like reference numerals denote the same or similar views throughout the several views.

BRIEF DESCRIPTION OF THE DRAWINGS

FIG. 8 is an exploded perspective view of the mask illustrating venting into the goggles.

FIG. 9 is a detail exploded perspective view of a portion of the mask illustrating the venting means.

FIG. 10 is a partial exploded sectional view of the mask taken along lines 10—10 of FIG. 8.

FIG. 11 is a partial (non-exploded) sectional view of the mask also taken along lines 10—10 of FIG. 8.

DETAILED DESCRIPTION OF THE PREFERRED EMBODIMENT

Figure 1:
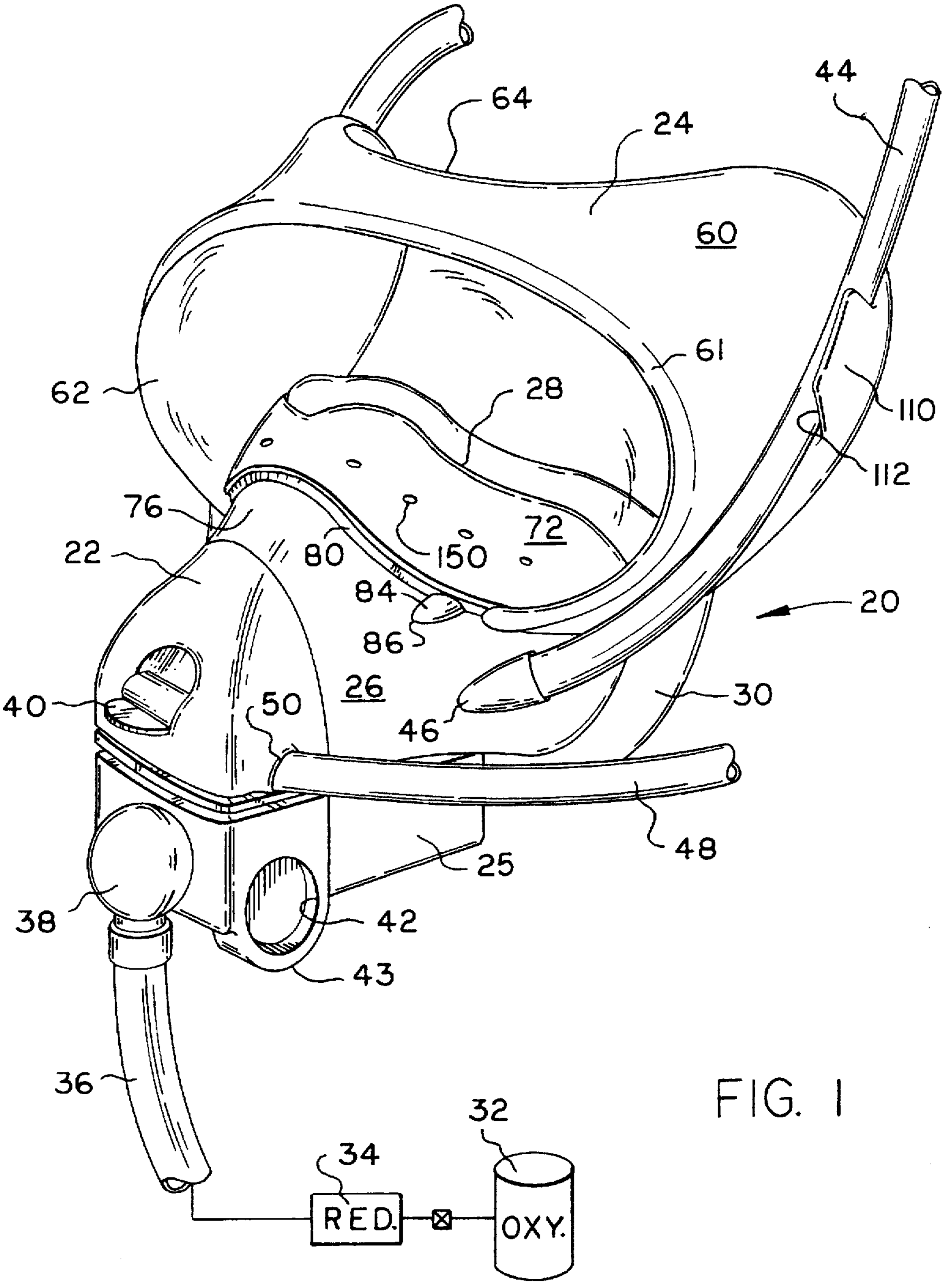
FIG. 1 is a perspective view, partly schematic, of a combination breathing mask and goggles which embodies the present invention.

Referring to FIG. 1, there is illustrated generally at 20 equipment to be donned by an airplane pilot for supplying breathing gas and for providing the ability to see in the event of the presence of smoke or fumes. The use of the equipment of the present invention is not limited to airplane pilots but may have other uses such as, for example, use by firefighters.

The equipment 20 includes an oral-nasal face mask 22 for covering the nose and mouth of the wearer for supplying breathing gas or oxygen for inhalation thereof and an eye enclosure 24 which may be called herein a "goggle" or "goggles."

The face mask 22 comprises a housing 25 to which is attached a molded body or enclosure 26 composed of plastic or other suitable air-tight material shaped to cover the mouth and nose of the wearer and having a generally triangular-shaped interface edge 28 to conform to the wearer's face. A suitable elastomeric sealing material, shown at 30 in FIG. 1 and not shown in the other FIGS. for ease of illustration, is suitably provided along the interface edge 28 to sealingly conform to the wearer's face to prevent loss of breathing gas from within the mask 22.

Figure 2:
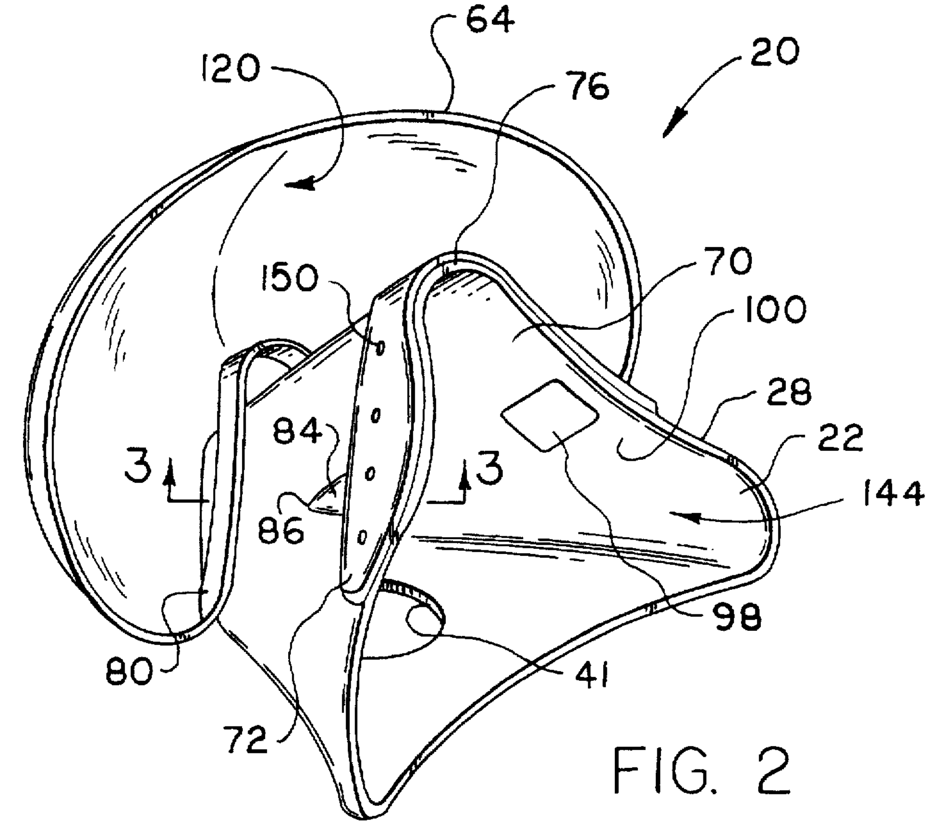
FIGS. 2, 4, and 6 are simplified perspective views thereof illustrating a sequence of attaching the goggles to the mask.
Figure 4:
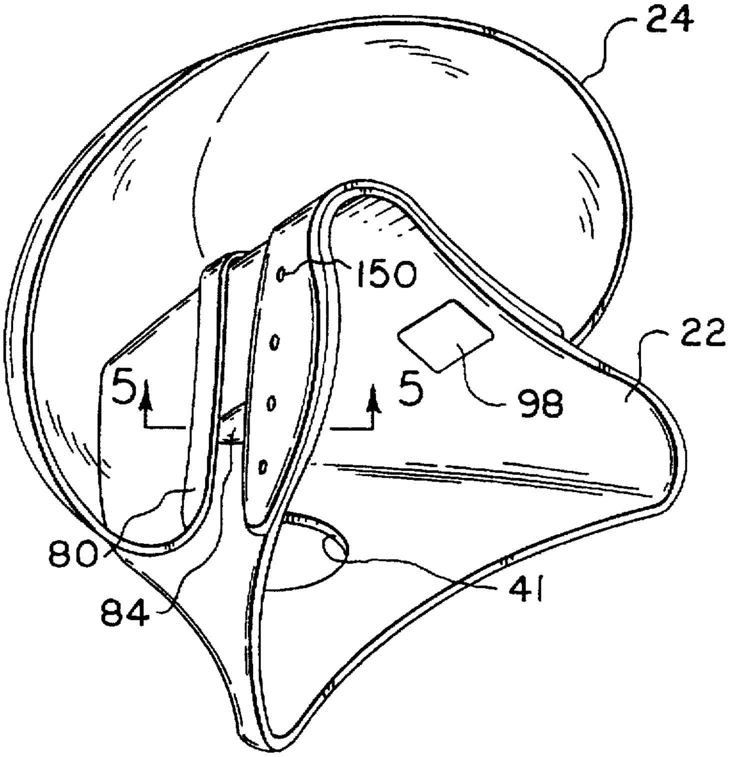
Figure 6:
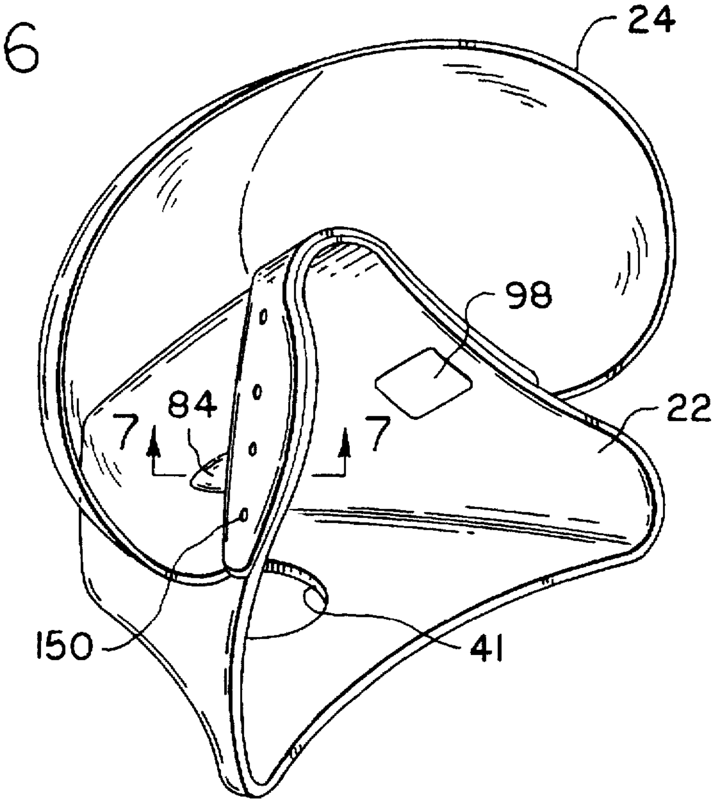

A source 32 of oxygen or other breathing gas is supplied via a conventional pressure reducing regulator 34 and through supply line 36 to a suitable inlet 38 for passage to a suitable breathing regulator (not shown) within the housing 25. A mode lever 40 is provided in the front of the enclosure 26 for switching the regulator between normal dilution, 100% oxygen, and emergency modes. A hole, illustrated at 41 in FIGS. 2, 4, and 6, is provided in the bottom of the enclosure 26 to provide flow communication with the breathing regulator within the housing 25. Depressions 42 in members 43 on opposite sides of the housing are provided to serve as finger grips. Tension straps 44 and 48 comprising a pneumatic head harness are swivelly or otherwise suitably attached at their ends to the enclosure 26, as shown at 46 and 50 respectively, on both sides thereof and are sized to encircle the wearer's head. They may be suitably connected to the oxygen supply to be inflated, thereby expanding, to allow donning of the mask 22. After the straps are placed in position, they are deflated to tighten about the wearer's head to draw the enclosure 26 tightly against the wearer's face to provide a seal between the elastomeric material 30 and the wearer's face. Inflation and deflation of the straps may be achieved by operating suitable valve means (not shown), using principles commonly known to those of ordinary skill in the art to which this invention pertains. For example, members 43 may be hingedly connected to the mask and attached to the valve means for operation thereof. It should, however, be understood that the head harness may be of any other suitable type. For example, the harness may comprise elastic straps and/or straps with buckles. As previously discussed, such a half face mask as so far described is well known in the art and can be provided using principles commonly known to those of ordinary skill in the art to which this invention pertains.

Face mask 22 is not a full face mask in that it does not cover the eyes. If there is smoke or fumes, the half face piece 22 may be left on and goggles 24 donned. Goggles 24 includes a shell or frame or lens holder 60 composed of silicone or other suitable air-tight material having sufficient rigidity to serve as a frame yet having sufficient softness to serve comfortably as a seal against the wearer's face. The degree of rigidity or softness of different portions may be adjusted by varying the thickness in accordance with principles commonly known to those of ordinary skill in the art to which this invention pertains. The goggles 24 also includes a see-through lens 62 composed of polycarbonate or other suitable material suitably sealingly mounted within a slot in a thickened bead 61 which is formed in the frame 60 or which may alternatively be a separate piece of elastomer or plastic strip. If desired, the lens 62 may have a suitable finish such as a hard coat or an anti-fog or anti-glare coating. The lens may be adhesively bonded to the bead 61 and perhaps also mechanically reinforced. The frame 60 is shaped to conform to the wearer's face and includes an edge portion 64 which serves as a seal against the wearer's face. Alternatively, the goggles may have a molded plastic frame with an elastomeric material 66 suitably provided along the edge for sealingly engaging and conforming to the wearer's face, as is well known in the art and as can be provided using principles commonly known to those of ordinary skill in the art to which this invention pertains. Alternatively, goggles 24 may be molded of a single piece of material such as, for example, an optically clear silicone or urethane which serves as a lens, a frame means for the lens, and a seal. The terms "frame means" and "frame", as used in this specification and the claims with reference to a goggle or goggles, are meant to refer to any structure supporting the lens including a structure which is integral with the lens and/or the seal.

Since a pilot may be busy with operating and/or emergency procedures, it is desirable that the goggles 24 be easily and quickly donnable with only one hand. In order that the pilot may do so, in accordance with the present invention the goggles 24 are strapless so that additional head straps may desirably be eliminated, and the goggles 24 and mask 22 are constructed so that the goggles 24 are detachably attachable to the mask 22 and so that the strap 44 may be coupled to the goggles 24 for holding the goggles securely and sealingly against the wearer's face. This allows the goggles 24 to be integrated as a unit with the mask 22. It should be understood that the present invention does not require the strap to be coupled to the goggles as long as means are otherwise provided for holding the goggles sealingly against the wearer's face.

Figure 3:
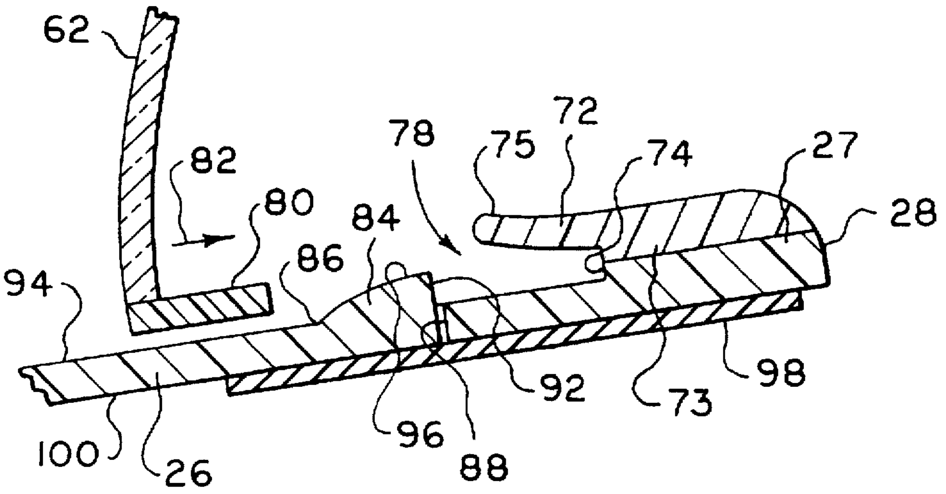
FIGS. 3, 5, and 7 are sectional views thereof taken along lines 3—3, 5—5, and 7—7 respectively of FIGS. 2, 4, and 6 respectively.
Figure 5:
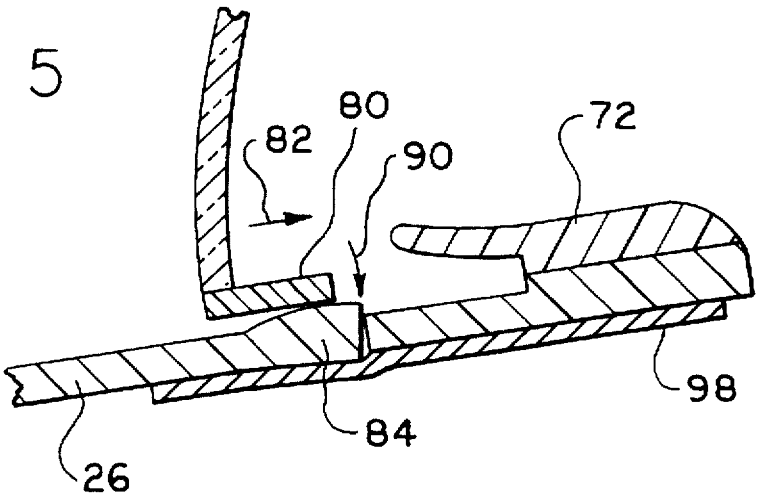
Figure 7:
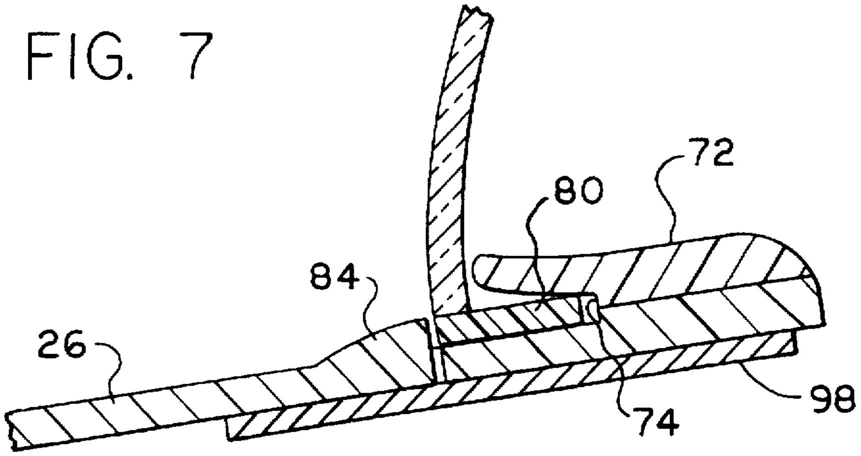

Referring to FIGS. 2 to 7, there is illustrated a preferred means for easily and quickly securely attaching the goggles 24 to the mask 22 by merely "snapping" the goggles 24 into attachment. FIGS. 2 and 3 illustrate the goggles unattached but in position to be attached to the face mask. FIGS. 4 and 5 illustrate the goggles being "snapped" into engagement with the face mask. FIGS. 6 and 7 illustrate the goggles sealingly and lockingly attached to the face mask. The upper or nose portion 70 of the mask 22 has a flap 72 attached thereto along the interface edge 28 and which extends forwardly therefrom to overlie the enclosure 26. The enclosure 26 is molded to have a raised portion 27 along the interface edge 28. The flap 72 has a corresponding raised portion 73 which mates with and is adhesively bonded, sonic welded, or otherwise suitably attached to portion 27, and the forward portion of flap 72 extends therefrom to be spaced from enclosure 26 thereby providing a groove, illustrated at 74, extending along the length of edge 28 along both sides of the mask from the upper nose bridge portion 76 and terminating part way down each side. For ease of illustration, the elastomeric sealing material 30 is not shown in FIGS. 2 to 7. If desired, the flap 72 may be molded integrally with enclosure 26. An entrance or opening 78 to the groove 74 is forwardly thereof and extends over the length thereof. A lower portion or flange 80 of the goggles frame 60 is sized in width and thickness and length to be snugly received within groove 74, as illustrated in FIGS. 6 and 7. If the goggles is found to have a separate seal, the flange or tongue 80 would not be provided with elastomeric sealing material since it is not intended to contact the face. The goggles 24 is attached to mask 22 by moving the goggles 24 rearwardly, as illustrated at 82 in FIGS. 3 and 5, and into the groove 74, as illustrated successively in FIGS. 3, 5, and 7.

Adjacent the entrance 78 to the groove 74 on opposite sides of the mask are a pair of buttons 84 (only one shown) which are integral with enclosure 26 and are molded therein to be enlarged so as to protrude outwardly of enclosure 26 so as to define raised portions thereof and thus act as a stop to forward movement of the goggles portion 80 out of the groove 74 whereby the goggles 24 may be securely or lockingly attached to the face mask 22. Each button 84 is molded to be only attached to enclosure 26 at its forward end 86 with its sides and rearward end being free of attachment to enclosure 26 thereby leaving a slot, illustrated at 88, in the enclosure 26 extending around the rearward end and sides of the button 84. Thus, the button 84 may be said to be cantileverly attached to the mask body. This allows flexing of the button 84 inwardly, as illustrated at 90 in FIG. 5, to permit the goggles portion 80 to be slid into groove 74. The rearward surface 92 of each button 84 is generally at right angles or normal to the outer surface 94 of enclosure 26 to prevent movement of the goggles portion 80 out of the groove 74, as seen in FIG. 7, without the wearer first pushing both of the buttons 84 inwardly to provide clearance for forward movement of the goggles portion 80 out of the groove 74. Each button 84 is tapered so that its thickness increases from its forward end at 86 to its rearward end at surface 92 so that its outer surface 96 gradually slopes outwardly from its forward end at 86 to its rearward end at surface 92 thereby allowing rearwardly-directed movement 82 of the goggles portion 80 to flexingly depress the buttons 84 inwardly to permit the goggles portion 80 to clear the buttons 84 and be slipped into groove 74 easily and quickly. After the goggles portion 80 is slipped into groove 74, the buttons 84 will flex outwardly to the position shown in FIGS. 3 and 7 to thereby restrain or stop the goggles portion 80 from moving forwardly out of the groove 74.

A patch or strip 98 of rubber or other elastomeric material is adhesively or otherwise suitably attached to the inner surface 100 of the enclosure 26 to sealingly cover each slot 88 to prevent the leakage of breathing gas from the mask 22. The patch 98 may alternatively be an inner extension of face mask seal 30. Strip 98 extends beyond the respective button 84 and corresponding slot 88 on all sides and is attached to have sufficient flexibility to permit inward movement 90 of the button 84, as illustrated in FIG. 5. As apparent from the above discussion, the buttons 84 are thus biased to return to the position shown in FIGS. 3 and 7, and the elastomeric strip 98 also acts as an elastomeric spring to bias or aid in biasing the respective button to that position.

Figure 12:
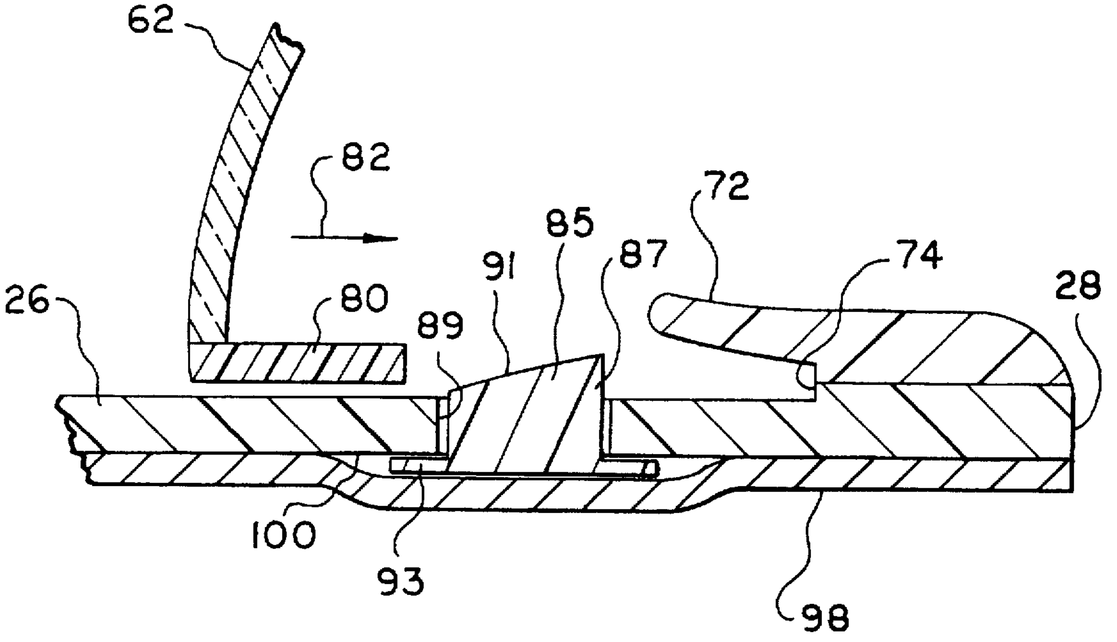
FIG. 12 is a view similar to that of FIG. 3 showing an alternative embodiment of the goggles attachment means.

Referring to FIG. 12, there is shown an alternative embodiment of the goggles attachment means wherein buttons 85 (one shown) which alternatively act as stops to forward movement of the goggles portion 80 out of the groove 74 are separate from (not integral with) enclosure 26 and composed of plastic or other suitable material. Button 85 has a body portion 87 which is received within enclosure opening 89 and having an inclined surface 91 corresponding to surface 96. The body 87 is held within opening 89 by a flange portion 93 which is sized to be larger than opening 89 and underlies surface 100. After placement of button 85 in the opening 89, the elastomeric strip 98 is attached to the enclosure 26 to permit inward movement of the button 85 for insertion of goggles portion 80 and to bias it to the position shown in FIG. 12.

As previously discussed, the goggles 24 are strapless. Referring again to FIG. 1, in order to hold the goggles 24 tightly against the wearer's face so that they may sealingly engage the wearer's face, in accordance with the present invention a pair of members 110 shown in FIG. 1 only and (only one shown) in the form of ears or hooks are molded to the goggles frame 60 to extend upwardly from and along both sides thereof and spaced therefrom to retainingly receive the strap 44 in the channel or groove, illustrated at 112, between the body of the frame 60 and each hook 110 to thereby utilize the tension in the strap 44 to hold the goggles 24 securely to the wearer's face. The positions of the ears 110 are selected to be in the normal path of the strap 44 about the wearer's head. After the goggles 24 are easily and quickly securely attached to the face mask 22, the strap 44 may be easily and quickly slipped over hooks 110 and retained in the grooves 112 to sealingly hold the goggles to the wearer's face and to the mask interface.

When it is necessary to don the goggles, it may be because the ambient atmosphere may contain smoke or gases which, if they accumulate within the space between the goggles and wearer's eyes, may be disabling and/or obstruct vision. In order to prevent such accumulation of gases within the goggles, in accordance with the present invention means are provided for venting breathing gases from the face mask 22 into the goggles 24 (into the space, illustrated at 120 in FIG. 2, bounded by the goggles and face of the wearer) to provide a positive pressure within space 120 to prevent entry of smoke and/or disabling gases.

Referring to FIGS. 8 to 11, there is illustrated a preferred embodiment of the venting means, it being understood that the venting means may be embodied otherwise, and such other embodiments are meant to come within the scope of the present invention. In accordance with the preferred embodiment, the enclosure 26 is molded to have an inwardly raised portion 122 rearwardly of the groove 74 and terminating short of the interface edge 28. A semi-cylindrical cavity, illustrated at 124, is provided in the outer surface 94 of the enclosure 26, rearwardly of the groove 74, and extending radially into the raised portion 122. A corresponding semi-cylindrical cavity, illustrated at 126, is provided in the flap 72 so that the cavities 124 and 126 together form a cylindrical chamber, illustrated at 128. The flap 72 and enclosure 26 are further molded with mating grooves, illustrated at 130 and 132 respectively, which together form an aperture, illustrated at 134, extending between and opening into cylindrical chamber 128 and groove 74. At the opposite or rearward end of chamber 128, the flap 72 and enclosure 26, which are bonded or welded or otherwise suitably attached together, are further molded to have respective grooves, illustrated at 136 and 138 respectively, which together form a blind aperture, illustrated at 140, extending rearwardly from and opening into cylindrical chamber 128. A plurality of perhaps three openings, illustrated at 142, are provided in the inwardly raised portion 122 to extend between and open into the space, illustrated at 144, within the face mask 22 and the cylindrical chamber 128 so as to route breathing gas from within the face mask space 144 into the cylindrical chamber 128. A pair of mating grooves, illustrated at 146 and 148 respectively, in the outer surface 94 of enclosure 26 and in the flap 72 together form a channel which opens into the cylindrical chamber 128 on both opposite sides thereof and extends parallel to the interface edge 28 and terminates blindly at each end. Spaced along the length of the channel 146, 148 are a plurality of holes or apertures, illustrated at 150, in the flap 72 which extend between and open into the channel 146, 148 and the goggles interior space 120. An additional aperture, illustrated at 152, in the flap 72 extends between and opens into the cylindrical chamber 128 and the goggles interior space 120. Thus, breathing gas from within the face mask space 144 may be routed through apertures 142 into the cylindrical chamber 128, then through aperture 152 and through channel 146, 148 and apertures 150, as illustrated by arrows 154, into the goggles space 120 to provide a positive pressure therein to advantageously prevent the accumulation of smoke and/or disabling gases therein. Apertures 150 and 152 also route the breathing gas so that it wipes the interior surface of the lens to prevent fogging thereof.

When the goggles are not being worn, breathing gas would undesirably escape into the ambient air and be wasted if not otherwise stopped. In order to prevent this from occurring, the face mask 22 is provided with a valve, illustrated generally at 160, which is actuated by the attachment of the goggles 24 to the face mask 22 for allowing breathing gas into the goggles space 120 for venting thereof. The valve 160 includes a cylindrical member or spool 162 adapted to fit within the changer 128 and having a seating surface 164 formed of a layer of elastomeric or other suitable sealing material for sealingly engaging the surface 166 containing apertures 142, as illustrated in FIG. 11, for preventing breathing gas from leaving the face mask 22. The valve includes a pair of shank portions 168 and 170 extending from opposite sides of seating member 162. Shank portion 168 is received within aperture 134 and extends into groove 74. Shank portion 170 extends into aperture 140 allowing seating member 162 to seat against surface 166 whereby the valve may be said to be closed (preventing release of breathing gas from within the face mask) and to move rearwardly therefrom whereby the valve may be said to be open (allowing breathing gas into the goggles space for venting thereof). The valve 160 is biased by means of spring 172, which is positioned around shank portion 170 between the seating member 162 and the rear surface of chamber 128, or by other suitable means to the closed position shown in FIG. 11 to prevent the escape of breathing gas from the face mask.

Movement, as illustrated at 82, of goggles portion 80 into slot 74 and past the buttons 84 to the position shown in FIGS. 6 and 7 to don the goggles 24 pushes the valve shank portion 168 rearwardly thereby pushing seating member 162 rearwardly against the force of spring 172 to unseat from surface 166 thereby opening the valve 160 to allow passage of venting gas through apertures 142 and into goggles space 120 for venting thereof, the venting gas providing a positive pressure in space 120 to prevent entrance of smoke and/or disabling gases and to prevent or reduce the formation of fog or mist on the inside of the lens. It can thus be seen that valve 160 will remain open as long as the goggles 24 are donned. When the goggles are detached from the face mask, the force of spring 172 will cause the valve member 162 to seat against surface 166 to close the valve so that breathing gas does not escape from the face mask.

Thus, it can be seen that the goggles are provided to be easily and quickly donnable by only one hand by snapping the goggles portion 80 into groove 74 with the buttons 84 securing the goggles portion 80 in the groove and with the action effecting opening of the valve 160 for admission of breathing gas to the goggles for venting thereof. The face mask harness strap 44 may then be easily and quickly lifted over the hooks 110 to be retained in the space between each hook 110 and the goggles frame to effect a sealing engagement of the goggles to the wearer's face. The goggles may be easily removed by disengaging the strap 44 from the hooks 110 then pushing inwardly on buttons 84 and sliding goggles portion 80 forwardly out of groove 74 and over the depressed buttons, the spring 172 effecting closure of valve 160 to prevent the escape of breathing gas. If desired, the face mask 22 and goggles may be stored already attached while not being worn so that they are equivalent to a full face mask ready to be conveniently donned as a unit.

It is to be understood that the present invention is by no means limited to the specific embodiments which have been illustrated and described herein and that various modifications thereof may indeed be made. For example, other means may be provided for attaching the goggles to the face mask or for coupling the face mask harness to the goggles or for supplying venting gas to the goggles. Such other embodiments are meant to come within the scope of the present invention as defined in the appended claims.

What is claimed is:

1. For use with a breathing mask which covers a wearer's nose and mouth and which has strap means for extending about the wearer's head for sealingly attaching the mask to the user's face, a strapless goggle comprising frame means, lens means, means for detachably attaching the goggle to the mask, and means on said frame means for co-operating with means on the mask for holding the goggle sealingly against the wearer's face.

2. A strapless goggle according to claim 1 wherein said means on said frame means comprises means for coupling the strap means to the goggle.

3. A strapless goggle according to claim 2 wherein said coupling means comprises members on said frame means for retainingly receiving the strap means between said frame means and said members respectively.

4. A strapless goggle according to claim 2 wherein said detachably attaching means comprises means defining a tongue interface member which is adapted to be receivable in a groove interface means in the mask.

5. A strapless goggle according to claim 1 wherein said detachable attaching means comprises means defining a tongue interface member which is adapted to be receivable in a groove interface means in the mask.

* * * * *